(12) United States Patent
Becker et al.

(10) Patent No.: US 8,392,218 B2
(45) Date of Patent: Mar. 5, 2013

(54) SEQUENTIAL CONTROL AND EXECUTION OF MEDICAL APPLICATIONS AT DIFFERENT WORKSTATIONS

(75) Inventors: Detlef Becker, Möhrendorf (DE); Karlheinz Dorn, Kalchreuth (DE); Christian Scharf, Aurachtal (DE)

(73) Assignee: Siemens Aktiengesellschaft, Munich (DE)

( * ) Notice: Subject to any disclaimer, the term of this patent is extended or adjusted under 35 U.S.C. 154(b) by 606 days.

(21) Appl. No.: 12/382,528

(22) Filed: Mar. 18, 2009

(65) Prior Publication Data

US 2010/0241443 A1    Sep. 23, 2010

(51) Int. Cl.
*G06Q 10/00* (2006.01)
(52) U.S. Cl. ................................. 705/3; 705/2
(58) Field of Classification Search .................... 705/2, 3
See application file for complete search history.

(56) References Cited

U.S. PATENT DOCUMENTS

| 2004/0267595 A1* | 12/2004 | Woodings et al. | 705/9 |
| 2005/0177399 A1* | 8/2005 | Park | 705/3 |
| 2009/0132586 A1* | 5/2009 | Napora et al. | 707/104.1 |

* cited by examiner

*Primary Examiner* — Robert Morgan
*Assistant Examiner* — Maroun Kanaan
(74) *Attorney, Agent, or Firm* — Harness, Dickey & Pierce, P.L.C.

(57) ABSTRACT

A process, a system and a computer program product and computer readable medium are disclosed for the sequential control and execution of a medical task. In at least one embodiment, the task is processed with the aid of a plurality of different, computer-implemented, medical-technical, stateful applications. In at least one embodiment, the invention uses a 3-layer software architecture including a data layer, a business logic layer, and presentation layer. With the aid of a central server, the option is provided of a one-time loading of the extensive datasets for a task and the applications for a task, so that the datasets and the applications are subsequently preserved for a user of the medical task. As a result, multiple waiting periods for the user are avoided.

27 Claims, 5 Drawing Sheets

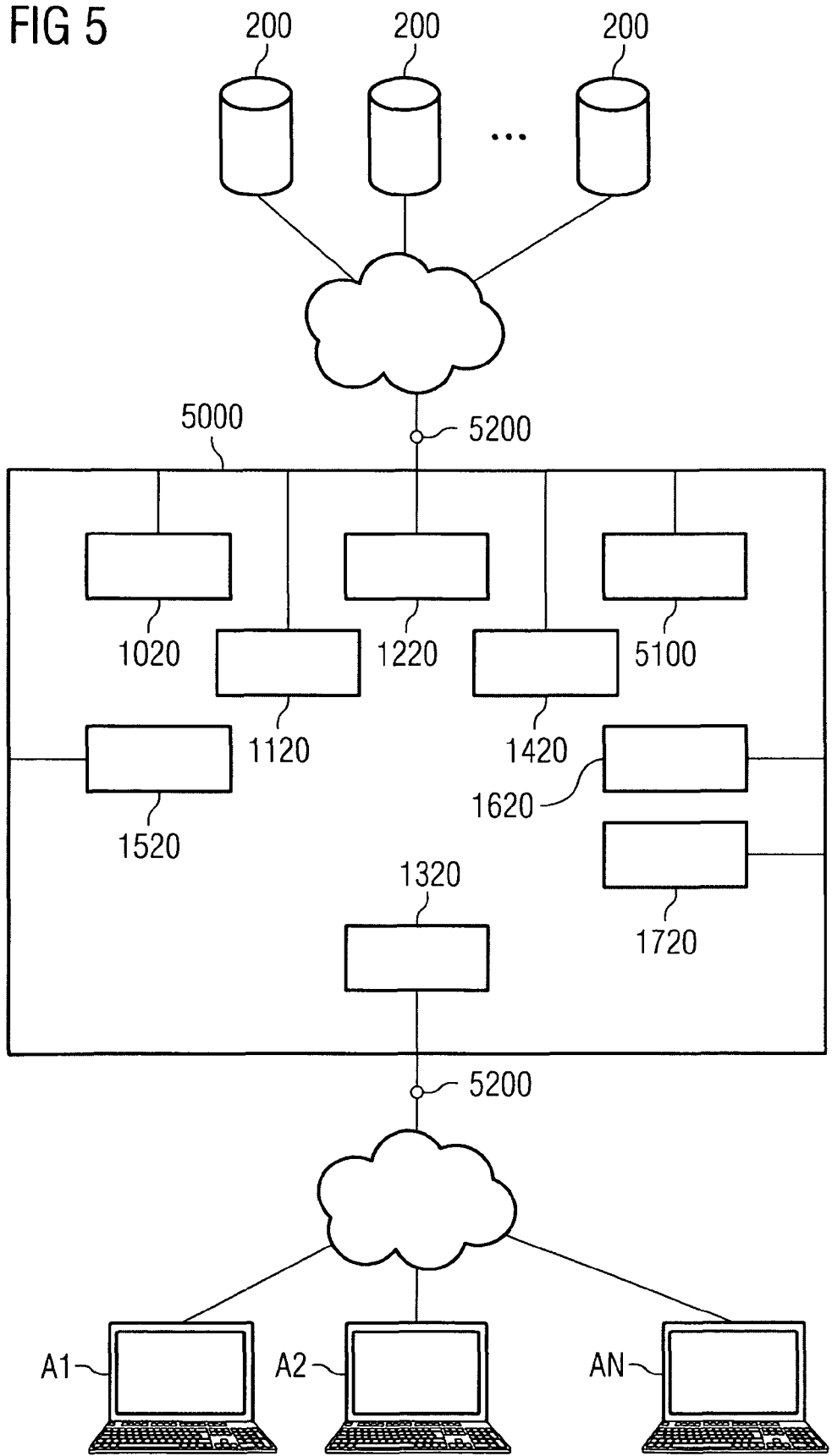

SEQUENTIAL CONTROL AND EXECUTION OF MEDICAL APPLICATIONS AT DIFFERENT WORKSTATIONS

FIELD

At least one embodiment of the present invention generally deals with the fields of data processing and medical technology. In particular, at least one embodiment relates to a computer-implemented process, a system and/or a product for the sequential control and execution of medical tasks with aid of computer-implemented applications, which may be based, for example, on a 3-layer software architecture and are managed by a central server.

BACKGROUND

Medical, clinical systems generally run a great many complex processes, which must be modeled through linking a large number of computer-implemented applications.

The applications generally relate to completely different uses, for example the data acquisition or the post-processing of the detected image data and/or the generating of a report (reporting).

As a rule, complex medical tasks can be modeled with a sequence of partial tasks, wherein a partial task can be executed by different users or optionally also by users in different user roles. For example, a physician in the role of a reporter should be able to read and process different datasets than a medical-technical assistant in his/her role.

The following scenario is intended as example for a reporting task. A reporting task is generally initiated by issuing a message, a so-called "requested procedure" message. A patient is then examined in a first step, for example with the aid of an imaging process (MR, CT, ultrasound etc.) and the obtained data are subsequently stored. Normally, this step is performed by a medical technical assistant (MTA) on a first work station. Following the completion of the examination, the data are processed, possibly in dependence on a specific clinical issue, which may relate to a cardiology analysis, a perfusion, a colonoscopy, or a selection of parts of a dataset. For some medical applications, it is helpful if the detected medical image data are emphasized and/or marked with optional measures, wherein this task is generally performed by a so-called super MTA on a second work station. The resulting data are also stored. Following the completion of the two aforementioned preparatory processing steps, a radiologist in the role of clinical reporter can then analyze the obtained data and the already reprocessed datasets for the purpose of writing a report.

Different steps of a medical task can be carried out on different work stations, wherein these steps can furthermore be executed with a time delay. For example, a radiologist could wait until the evening to prepare reports of all cardiology analyses made during the day.

In the same way, it is possible to sequentially execute all steps of a medical task, wherein this direct execution of the individual steps can be of interest, in particular in emergency case scenarios. For an emergency case scenario, it is furthermore conceivable for a radiologist to realize all steps in order to save time.

The aforementioned example shows that from an information-technology point of view, it is no trivial task to interconnect the different applications and to execute these applications with the aid of different users at different work stations, as well as to provide the necessary resources, including the required datasets.

Until now, so-called stateless applications were generally used for this, for example web applications. It is characteristic for stateless applications that there is no provisioning of the processed data and the results achieved with the applications. For medical technical applications, which generally resort to comprehensive image datasets, the use of stateless applications is not advantageous. With stateless applications, the system performance gets worse for a user when loading comprehensive image data because of the longer waiting times.

Insular solutions were also frequently used in the past, so that one application was generally run independent of other applications. The steps taken so far have clear disadvantages and, in particular, result in the loss of performance during the daily operations.

SUMMARY

In at least one embodiment of the present invention, a path is shown for the flexible and variable control of a medical task that is implemented by several computer-supported applications. In particular, it should also be possible during the operation to adjust on which work stations a user interface (within the meaning of a presentation logic) for the respective application must run and on which work stations the actual application (within the meaning of a business logic for the application) must run, wherein different users can use different applications and wherein several applications can run parallel and several datasets can be processed parallel.

At least one embodiment of a solution is described in the following with respect to the process. Features, advantages or alternative embodiments mentioned in this connection must also be transferred to the other claimed subject matters (system and product) and vice versa. In other words, the actual claims with the features described and claimed in connection with the process, can be modified further. The respective functional features of the process are embodied as corresponding representational system modules, in particular as hardware modules and/or software modules.

In at least one embodiment, a process is disclosed for the sequential control and execution of a medical task, which is processed with the aid of several different computer-implemented medical-technical stateful applications, wherein the applications are respectively based on a 3-layer software architecture, comprising:

a data layer with a number of different datasets;

a business logic layer with a number of business logic processes, wherein a business logic process respectively implements an application, and wherein several instances of a business logic process can be run parallel;

a presentation layer with a number of presentation-logic processors for displaying datasets within the framework of executing the associated business logic processes;

a central server that realizes the following process steps:
   determining the applications required for executing the medical task, as well as their business logic processes;
   determining the datasets required for the task and loading these datasets one time, as well as providing the loaded datasets automatically to all other processes within the framework of executing the task;
   determining the work stations needed for executing the application on which at least one presentation logic process is to be displayed
   dynamically interconnecting or linking of the loaded datasets with at least one business logic process or with precisely one instance of at least one business logic process;

interconnecting of the respective presentation logic process for the respectively determined application with at least one instance of the business logic process for the determined applications;

executing of the specified business logic and presentation logic processes and storing of the datasets;

wherein respectively one presentation logic process is displayed on at least one work station and wherein at least one work station displays a presentation logic process, and wherein after executing a business logic process, the datasets processed by the business logic process are automatically stored and automatically transmitted to at least one of the following business logic processes for the further execution of the task, without having to load the datasets again.

The terms used within the framework of embodiments of this invention are explained in further detail in the following.

Sequential control in this connection refers to the control of all processes, which are relevant within the framework of executing this task. It comprises all applications, the managing of the applications, the managing of the necessary datasets, and the communication between the individual applications, as well as the managing of the necessary resources. The sequential control therefore has a time component and a content component. The "time component" refers to the timely control of the interconnection of the individual applications, which is monitored, controlled and/or managed. The "content component" relates to that part of the sequential control, which controls the coordination of the individual applications in the content plane. One characteristic of the sequential control according to the invention is that is relates to the complete task and thus comprises the execution and/or control of all applications that are part of the system. The sequential control is connected to the development environment and to the run-time environment. The connection to the development environment is that it is predetermined which applications are linked in what way for executing the respective task. The connection to the run-time environment means that it is possible to adjust even during the operation which presentation logic must run on which work station and, for example, which computer (work station or central server) is used to execute the respective business logic. In other words, the (dynamic or static) behavior preferably occurs during the run time.

Executing the medical task refers to running all processes that are required for the complete processing of the medical task. It can relate to executing individual applications, parts of individual applications, the forwarding of messages (for example the results of the individual applications), the storage of datasets and making these available to subsequent applications, as well as to display the required presentation logic processes. Several tasks can furthermore be run parallel (e.g. a colonoscopy for patient A and parallel thereto the reporting for patient B).

A task can therefore be a reporting task, a diagnostic task, a post-processing task, or a task with optional content.

An application, in at least one embodiment, is a computer-implemented use in the medical-technical field. According to one example embodiment of the invention, only stateful applications are used. In contrast to stateless applications, the concept of the stateful applications is directed toward storing a state of the datasets (which it processes), as a rule via more than one user interaction. In other words, all datasets generated after each individual processing step for the application can be made available. The applications are made available based on a 3-layer software architecture, which distinguishes between the data layer, the business logic layer, and the presentation logic layer. The business logic is used to implement the actual application while the presentation logic functions as user interface and is intended for the display of datasets relative to the application and/or relative to the respective business logic process.

According to this software architecture model, the presentation of the data is uncoupled and/or separated for each application from the actual data processing. A presentation logic process is therefore as a rule completely independent from a business logic process and can run on the same computer, but also on different computers. For example, it is conceivable that the business logic process runs on the central server while the associated presentation logic process runs on a respective work station.

According to one example embodiment, respectively one instance of a business logic process is unambiguously assigned to a dataset, wherein this dataset is patient-specific. In other words, a patient-specific dataset is assigned to precisely one instance of a business logic process while other instances of the same business logic process can process other patient-specific datasets. If only one patient "is to be processed," then only one instance of a business logic process is loaded. If several patients are to be processed, then several instances of a business logic can also be loaded parallel (meaning at the same time).

According to a concept for an embodiment of the present invention, it is possible for respectively one application to be used by different medical users and/or by users in different user roles (MTA, reporting physician, etc.). In addition, the respective applications can be controlled and/or used from different work stations. Owing to the 3-layer architecture, it is possible to separate the executing of the business logic processes from the executing of the presentation logic processes. In other words, the business logic of an application can be run on a different computer than the associated presentation logic, thus advantageously providing a higher flexibility of the sequential control.

The central server as a rule is a computer with the highest possible number of resources (CPU, memory, etc.) for executing the aforementioned steps of determining and interconnecting. Alternatively, it is possible for the central server to run partially or completely on a work station, wherein the central server can also be embodied as external instance and can be integrated into the system via a communication-technical link.

The work stations are preferably computer-supported work stations with different configurations, which include laptops, work stations, thin/thick clients, portable devices such as the PDAs and the like.

The term "interconnecting" refers to the creation of logical connections. The interconnecting therefore relates to the assigning of individual elements from the different layers of the 3-layer software architecture. Thus, a dataset from the data layer must be linked or connected to at least one business logic process of the business logic layer and a business logic process must be connected to an associated presentation logic process. The term "dynamic" in this connection means that a variable interconnection of the involved elements is possible. For example, a business logic process can be interconnected dynamically with a presentation logic process. In other words, it is thus possible to indicate during the run time, for example, on which work station the respective business logic process must be executed and/or controlled.

According to one example embodiment, the respective presentation logic processes and the respective business logic processes are also dynamically interconnected. As a result, a variable association between business logic process and presentation logic process is planned. Alternatively, it is possible to turn off this variable association and to provide a fixed/rigid association between business logic process and presentation logic process.

According to one example embodiment of the invention, respectively one application is assigned a specific user role. The user role relates to an authorized function of the respective user and/or processor. Examples for a user role are MTA, super MTA, physician, reporting physician, system administrator, and the like. A user who meets this user role (for example is assigned this user role ahead of time) is consequently authorized to execute all or only specific applications. For example, this feature permits specifying that the physician in the user role of report writer is basically authorized to access all patient data while the MTA in its user role can view and process only some of these data. A user role is generally authorized to execute at least one business logic process. As a result, the respective user is also authorized to operate and/or control the respective business logic process that is assigned to the respective presentation logic process. Assigning user roles to respectively one application advantageously achieves that the authorization and/or non-authorization is not given to a single user, but to a group of users, namely those who meet this user role. In addition, it is advantageously possible to authorize or prohibit access to specific datasets by giving authorization to the respective user in the user role only for executing the respective presentation logic from the presentation logic layer.

According to a different advantageous embodiment of the present invention, a so-called work list can be displayed for a user in a user role, thus providing the user at all times with an overview of which business logic processes must still be executed. At least one embodiment of the invention thus makes it possible to provide a user-specific view of the respective task. In other words, it is possible to provide data that show which user must still execute what processing steps in order to be able to successfully conclude the task. For example, parallel reports must be prepared for several patients during the clinical workday, which means that several tasks must be executed parallel. Several patients are therefore assigned to several reporting tasks. In that case, a MTA would have the following work list: "record datasets for patient A," "record datasets for patient B." "record datasets for patient C," . . . "reprocess datasets from patient A," "reprocess datasets from patient B," "reprocess datasets from patient C," and the like. According to this embodiment, it is possible to draw up all work lists for all user roles and display these (possibly after being filtered).

According to yet another advantageous embodiment of the present invention, a status is detected with respect to the sequential control and execution of the medical task. This status can be called up, for example, on a selectable work station via a browser application. As a result, a user authorized to call up the status can call up the respective task. A status could comprise the following information: task X comprises the applications X1, X2, X3. The application X1 involves the business logic process G1, the application X2 involves the business logic process G2 and the application X3 involves a business logic process G3. The presentation logic process P1 is interconnected with the business logic process G1, the presentation logic process P2 is interconnected with the business logic process G2, and the presentation logic process P3 is interconnected with the first instance of the business logic G3. The presentation logic process P4 is interconnected with the second instance of the business logic G3, wherein the business logic process G3 is made available in two instances. Of the business logic processes G1, G2, G3 and G4, the processes G1 and G2 have already been processed.

Alternative embodiments can comprise the status of additional information. This feature has the advantage of improved user friendliness since the user can obtain more transparency concerning the work.

According to a different advantageous embodiment of the invention, the status is to be processed further, in particular filtered, by the central server, thus making it possible, for example via the browser application, to call up the respective state of a reporting task and thus the condition of the respective patient. A user can thus advantageously derive the information on which steps must still be carried out for the task and which have already been processed. A result set (result of the respective task) can be filtered, for example based on the user role. The status can consequently be filtered based on the user roles, which are necessary for processing the respective business logic processes for the task. In other words, it means that only those processing steps are displayed for a MTA, which can actually be executed by the MTA and/or for which the MTA has authorization.

One advantageous modification of at least one embodiment of the invention provides that a task overview is made available and/or is displayed during the selection of a medical task, which comprises among other things information on which datasets and/or which business logic processes and which presentation logic processes are presently loaded and/or must still be loaded for executing the medical task. This feature provides an additional control option and higher flexibility.

According to one example embodiment of the invention, all process steps and especially the interconnecting of the respective elements from the various layers are realized automatically. This feature has proven to be very advantageous in cases of a fixed and/or rigid hospital sequence. In other cases, a semi-automatic process can also be made available, so that it will be possible to intervene manually in the interconnecting process.

The central server for the example embodiment is embodied as central instance and administers all information required for executing the medical task, including the task itself, the business logic processes, the presentation logic processes, the work stations and the interconnections. This information is managed in the central server. In addition, the central server can also add, delete and/or modify individual presentation logic processes and/or individual business logic processes. The computer-implemented system can therefore be advantageously modified at any time for executing the medical task.

The central server preferably comprises a control interface for exchanging control messages, which allows a user (e.g. a system administrator) to make adjustments in view of the sequential control. For example, the user could specify a manual interconnecting of elements from the individual layers. It is also conceivable that messages are exchanged via the control interface, in particular warning messages, for example if the respective task could not be executed successfully.

According to one example embodiment of the invention a business logic container process is provided for all business logic processes and, in the same way, a presentation logic container process is provided for all presentation logic processes. The respective business logic process and the presentation logic process are started with the aid of the individual container process. Each application requires a so-called father process for loading it. This father process and/or container process takes care of all communication with the central server. A container process is therefore a run-time environment for the respective business logic and/or the respective business logic process or the presentation logic process. A processing container consequently is provided to generate a presentation logic and link the presentation logic to all its processes within the business logic. For further information we also point to the "dynamic assembly" concept, known from the field of computer programming.

The linking or interconnecting process is preferably monitored, thus making it possible to detect errors resulting from an incorrect manual interconnecting of the respective elements from the different layers and to point this out to the user.

According to another feature of at least one embodiment of the invention, a permanent monitoring of the performance of executing the respective task is planned. For example, a performance problem can develop because a great many parallel-running applications occupy important system resources. A different aspect of at least one embodiment of the present invention therefore provides that a business logic container process, which has not been interconnected for a longer period of time and/or for a pre-configured time period with a presentation logic process, can be used for a different reporting task and/or for another business logic.

An already loaded business logic process can therefore be used for a different task, so that no new instance of the respective business logic process must be generated. The central server in that case triggers the business logic process, identified as "not used for a longer period of time," to persist in its state (e.g. in the file system or in a database). The central server then informs the respective business logic process of the parameters for the new task and/or the new patient reporting requirement. As soon as the business logic process has stored its state, it transmits an unambiguous reference to the storing of this state to the central server, so that the central server can, if necessary at any time move another instance to the specific state in order to continue with the reporting task.

According to this aspect, the total use of resources for the system can be influenced advantageously, meaning independent of the number of tasks that have arrived. This feature makes it possible to weigh between performance and system resource use. In other words, the sequential control can be controlled in view of the performance and in view of the system resource use.

As an alternatively to the aforementioned, changeable connection between business logic process and presentation logic process, it is possible according to another variant of at least one embodiment of the invention to interconnect the respective presentation logic process rigidly and/or fixedly with the associated business logic process. The dynamic interconnection is thus turned off, meaning there are as many instance of an application (comprising presentation logic process and business logic process) as there are users working on the system, regardless of the number of tasks.

Whenever a new task is generated by a user, the executing business logic is stimulated by the central server to persist in its present state and is then moved to the new task context by the central server.

A different aspect of at least one embodiment of the present invention is seen in the fact that several medical tasks can be realized parallel. It is advantageously possible to predetermine the number of medical tasks can be realized and/or managed parallel, thus making it possible to specify ahead of time an upper capacity limit.

To maintain a more flexible system on the whole, the central server can be run at least in part on one of the work stations, which makes sense in particular if the connected work station has comprehensive resources. Alternatively, the central server can also be run on a separate work station, whereas the actual work stations are embodied as thin clients.

According to a different aspect of at least one embodiment of the invention, the respective dataset that is generated and/or changed by respectively one business logic process is also automatically stored. As a result, all processing steps connected to executing the task are stored. In other words, the executing of a business logic process leads to a specific result (e.g. the dataset is changed by the respective business logic). This result can then be automatically forwarded to the following business logic process, or the result can alternatively also be forwarded to several business logic processes. The latter makes sense if there are several business logic processes requiring the same input data.

Owing to the 3-layer software architecture, the executing of the business logic process basically does not depend on the executing of the respective presentation logic process. In other word, the presentation logic process can be run on a different computer/work station than the associated business logic, wherein individual instances of the business logic processes, individual business logic processes and/or individual presentation logic processes can also be run on the central server.

Thus, a business logic process and/or a presentation logic process can run on the central server and/or on a work station. Depending on the current workload of the respectively involved computer (work station and central server), the work load can therefore be taken into account and distributed dynamically. This information (which processes run on which computers) is preferably made available, wherein the aforementioned applies to the business logic processes as well as the presentation logic processes.

At least one embodiment furthermore involves a computer program product. At least one embodiment furthermore involves a system.

One aspect of at least one embodiment of the present invention is that for each task it must be determined only once which datasets are required for executing the task and that these datasets are loaded one time. If different business logic processes must be realized with these datasets, it is no longer necessary to load the datasets so-to-speak multiple times and separately for the different business logic processes. The datasets, once loaded, are made available to all instances (in particular to the specific business logic processes) which require these datasets for executing the task. For example, if a dataset for the patient "Müller" must be detected with a first business logic process and must then be re-processed with a second business logic process, it is no longer necessary according to the invention to load the dataset "Müller" twice. The patient dataset is loaded only once and is then made available to both applications. If the second application requires data from the first application, then the results (meaning the data) from the first application are automatically provided to the second application.

It is also advantageous to have a 1:1 coordination between a patient dataset and an instance of a business logic process, thus keeping the programming of the respective applications very simple. The respective business logic process is loaded with the specific datasets for the patients and remains in this state until the task has been completed. The respective presentation logic process can then be interconnected and/or linked flexibly with different instances of this business logic process. For this example embodiment, we can stay with the programming paradigm based on the assumption that in each case, one application uses precisely with one patient dataset at a time.

A further advantage of the solution according to at least one embodiment of the invention is that after executing an application, a user can continue and move directly to the processing of the following patient-specific dataset, so as to realize the partial step required for this patient (user-specific) within the framework of the task. The patient data need not be loaded again because they are already available on the central server, following a one-time loading. In other words, one and the same presentation logic process can be used sequentially for several patient-specific tasks. The performance is thus improved noticeably for the user because it is no longer necessary to again load the presentation logic for a new patient. According to at least one embodiment of the invention, it is only necessary to interconnect the presentation logic process with the respective business logic process, wherein the datasets for the respective business logic have already been loaded and can be made available immediately.

The dataset preferably comprises a plurality of different documents from a patient file. A patient file can include several folders, for example relating to different examinations within the framework of different illnesses.

The above-described embodiments of the process according to the invention can also take the form of a computer program product, wherein the computer is triggered to realize the above-described process according to the invention if the program is run on the computer and/or a processor for the computer.

An alternative solution of at least one embodiment calls for a storage medium, which is intended for storing the above-described, computer-implemented process and can be read by a computer.

In addition, it is possible to embody individual components for the above-described process in the form of a unit ready for sale and to embody the remaining components in a different unit ready for sale, so-to-speak as a distributed system.

BRIEF DESCRIPTION OF THE DRAWINGS

Reference is made in the following to the enclosed Figures, which represent parts of the disclosure for embodiments of the invention.

FIG. 5 shows a system according to one embodiment of the present invention.

DETAILED DESCRIPTION OF THE EXAMPLE EMBODIMENTS

Figure 1:
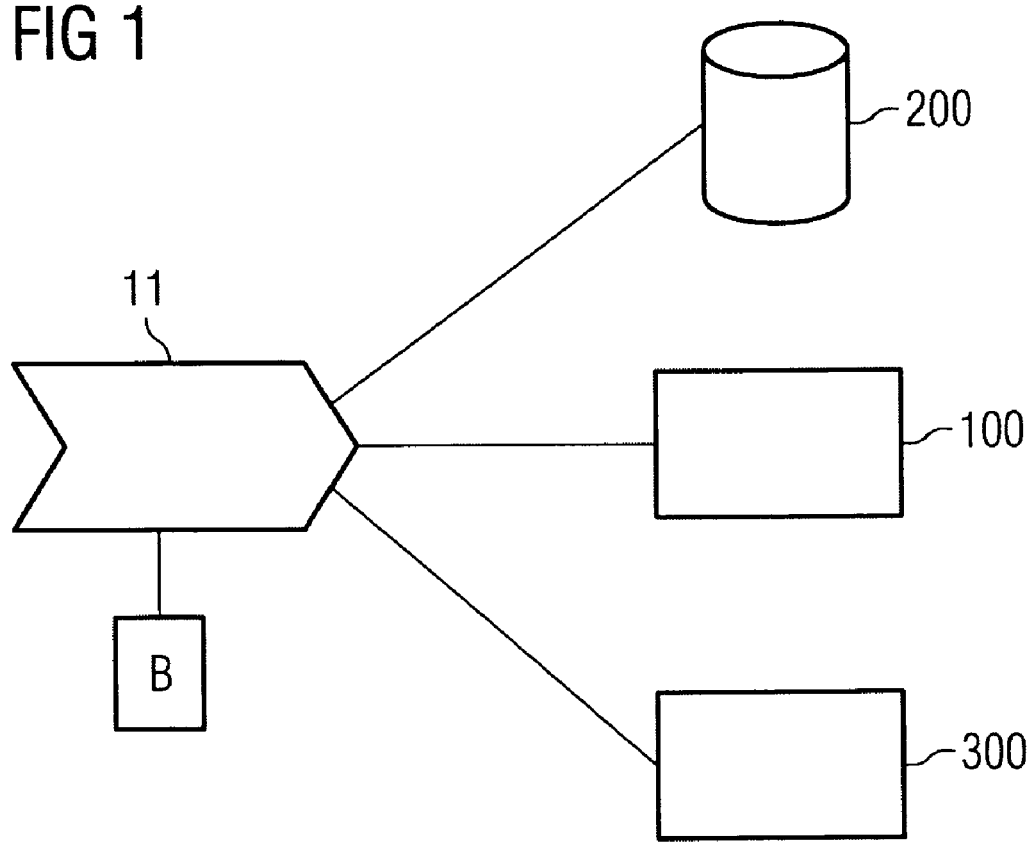
FIG. 1 shows the 3-layer architecture of an application according to one embodiment of the invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The selected examples for the following embodiments of the invention are explained below with reference to the drawings. One skilled in the art can see from the disclosed content that the following explanations for the example embodiments of the invention are only intended for the purpose of illustration and not to restrict embodiments of the invention.

An embodiment of the present invention proposes a process for the sequential control and for executing a medical task 10, wherein this medical task 10 could refer, for example, to an examination of the abdominal cavity of a patient admitted to the hospital. According to an embodiment of the invention, the medical task 10 is represented as a plurality of different, computer-implemented medical-technical, stateful applications 11. Depending on legal guidelines, for example, the medical task 10 can be modeled by a sequence of applications 11. According to an embodiment of the present invention, the application 11 as individual step for the medical task 10 is modeled with a 3-layer software architecture.

FIG. 1 illustrates the 3-layer software architecture for the applications 11 of the medical task 10. The application 11 comprises a dataset 200 in a data layer, which represents the first layer of the 3-layer software architecture. The second layer of the 3-layer software architecture is a business logic layer. A business logic process 100 is assigned to the application 11. Individual tasks to be solved with the application 11 are modeled in the business logic processes 100. In an embodiment, the business logic process 100 is separate from the dataset 200 that is assigned to the application 11. Furthermore provided is a presentation layer for representing and/or displaying results and/or for executing partial tasks presented by a user via the business logic processes 100. A presentation logic process 300 makes possible the interconnection between a user and the business logic process 100.

It must be mentioned here that the presentation logic layer is separate from the business logic layer and the data layer, thus considerably simplifying the programming of the applications 11 within the medical task 10. An embodiment of the invention furthermore provides that each application 11 is assigned a user role B. With the aid of the user role B, it is possible to specify which user groups and/or user roles B are authorized to execute a specific application 11 within a medical sequence and/or a medical task 10. These user roles can be medical-technical assistants, for example, super MTAs that monitor several medical-technical assistants or they can also be radiologists. Assigning the user role B to the applications 11 and thus to the business logic process 100 and the presentation logic process 300 allows determining which business logic processes 100 and/or presentation logic processes 300 of an application 11 a MTA in the user role B2 is authorized to view and process. For example, a user in the user role B can only run those business logic processes 100 and/or presentation logic processes 300, which the user in the user role B is authorized to execute and/or to display. Assigning applications 11, and thus also steps within a medical task 10 in this way to a user role B, meaning the assignment of applications 11 to a user role B, for example, ensures that only a radiologist can issue a report and not a MTA who is not authorized to do so because of education or based on legal guidelines. It can thus be ensured that only users in the user role B, which are authorized to execute the applications 11 within the medical task 10, can actually realize this task.

With a modeling of this type it is thus possible to prove that within the hospital operations, only sufficiently qualified users will be able to execute the operating steps, meaning to run the respective applications 11 for the medical task 10, in the form of the business logic process 100 or the presentation logic process 300 assigned to the application 11.

Figure 2:
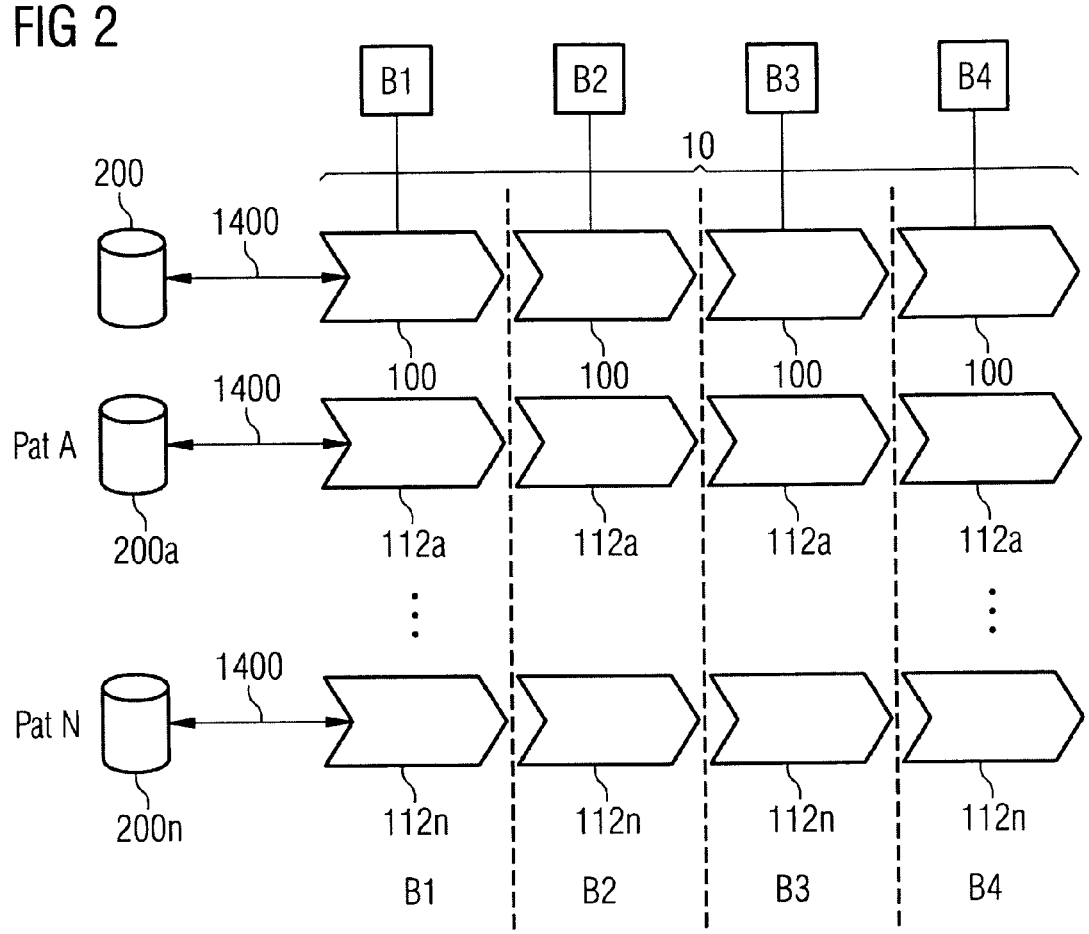
FIG. 2 shows a medical task represented by several business logic processes and their instances.

FIG. 2 shows in the upper line an example of a medical task 10, composed of several business logic processes 100, wherein each of the business logic processes 100 solves a partial task of the medical task 10. If we assume that the medical task 10, as shown in upper lines of FIG. 1, represents an abdominal cavity examination, then the first business logic process 100 could involve the scanning of the abdominal cavity by a nurse in the role as user B1. The user role B1 assigned to the first business logic process 100 would then be the nurse user role B1. An abdominal cavity examination of a patient could involve an ultrasound examination carried out by an MTA as the following step within the sequence of steps.

This ultrasound examination could be modeled as the second business logic process 100 within the medical task 10, as shown in the upper line in FIG. 2. The user role B2 of the second business logic process 100 would then be the role of a MTA. For example, the MTA could perform an ultrasound examination of the kidneys and the gall bladder. In the following third step of the clinical sequence, a super MTA in the user role B3 as super MTA could then evaluate the ultrasound images of the patient.

The evaluation of the ultrasound images is based on the ultrasound examination data obtained in the second processing step by the MTA in the user role B2. That is to say, the patient data generated during the second step are made available to the following steps and/or the following business logic processes 100 of the medical task 10. For example, it could be determined during the evaluation of the ultrasound data whether the patient's kidney is blocked and whether kidney stones can be detected. The data and/or the datasets 200 are kept available within the data layer of the 3-layer architecture. Each of the business logic processes 100 within the medical task 10 can store the recorded datasets 200.

In particular the applications 11 and thus also the business logic process 100 are implemented as state-based applications. It means that datasets 200, once they are loaded, are preserved by the business logic process 100. Since a great many data are collected during an examination of patients, it is advantageous if the datasets 200 need to be loaded only once by the business logic process 100. An embodiment of the present invention makes this possible, as explained in the following.

The fourth step within the medical task 10 could comprise, for example, a report by an internist in the user role B4 as internist B4. The report issued by the internist will be based on the previously collected data, meaning it will be based on the result of the scanning of the abdominal cavity by a nurse or on the ultrasound data, as well as on the evaluation of the ultrasound data by the super MTA. As a rule, only the last steps of the medical task 10 are shown to the internist in the user role B4. If several patients with abdominal cavity problems are admitted to the hospital, the process according to an embodiment of the invention must ensure the execution of the medical tasks 10 and the sequential steps. According to an embodiment of the invention, it is provided that several instances 112 of the business logic processes 100 for the medical task 10 can be loaded and run.

According to an embodiment of the present invention, precisely one of the instances 112 of a business logic process 100 is assigned to precisely one patient. It means that for each patient, instances 112 of the business logic processes 100 belonging to the medical task to be carried out for a patient are started, as indicated in FIG. 2. The upper most line shows the general description of a medical task 10, for example an abdominal cavity examination. If several patients are admitted, as indicated in FIG. 2 with patient A, . . . patient N, for which a medical task 10 is requested as a procedure, then the present invention makes it possible to start for each of these patients the instances 112 of the business logic processes 100, which participate in the selected medical task 10.

The respective instances 112 of the respective business logic processes 100 are therefore preserved for each patient, along with the required datasets 200. In at least one embodiment of the present invention, the business logic processes 100 and thus also the instances 112 of the business logic processes 100 are assigned precisely to one patient and thus precisely to one of the datasets 200. This design facilitates the programming of the applications 11 for modeling the medical tasks 10. In a hospital, many patients requiring the same medical task 10 oftentimes are admitted simultaneously.

The decision to start for each of the admitted patients a separate instance 112 of the business logic processes 100 that are involved in the task 10 simplifies the programming. The business logic processes 100 in that case must only manage respectively one dataset. On the other hand, if only one process were started for managing with its applications all abdominal cavity examinations of all patients, then the management and assignment of the datasets 200 to the correct patient would be very expensive and involved. In particular, such a programming approach would be subject to errors. For that reason, it is advantageous to assign a dataset 200 to precisely one medical task 10, meaning to precisely one patient for which a medical task 10 is realized by the instances 112 of the business logic processes 100 that participate in the task 10.

Each business logic process 100 also represents an instance 112 of the business logic process 100. If several medical tasks 10 are requested as procedure, several instances 112 of a business logic processes 100 participating in the task 10 are kept ready. For that reason, the instance 112 of a business logic process 100 and the business logic process 100 are viewed as nearly synonymous. An alternative view would be to understand the business logic process 100 as abstract description of what the application 11 achieves. That could even be a text-type description or a description that follows from legal guidelines. A concrete dataset 200 of a patient is not yet assigned to a business logic process 100.

In contrast to the business logic process 100, an instance 112 of a business logic process 100 is a concrete implementation of the abstract business logic process. This concrete implementation can, for example, be a computer implementation.

In any case, the business logic process 100 and the instance 112 of a business logic process 100 always represent the associated application 11 within the medical task 10.

As explained below, the invention additionally provides for a dynamic interconnecting 1400 of the datasets 200 with the business logic processes 100, as indicated in FIG. 2.

Assigning the user role B to each of the business logic processes 100 makes it possible to display for a user, in the user role B, only those applications 11 which the user is authorized to execute in the user role B. For example, a nurse in the user role B1 in FIG. 1 would see only those applications 11, which the nurse can realize, such as the scanning of the abdominal cavity. A work list for a user in a user role B can therefore be easily generated from the selected software-architecture for the system. The individual business logic processes 100 within the medical task 10 are generally processed sequentially. However, it is conceivable to interrupt the sequential processing, for example if a patient is admitted as emergency patient. In that case, the internist in the user role B4, in the fourth step for reporting the abdominal cavity examination, could have immediate access to the results obtained during the first or the second step. It is furthermore conceivable that the internist himself realizes these steps in order to save time.

Since a plurality of data and/or datasets 200 are collected when processing and/or executing the sequence of steps for the medical task 10, a long waiting period may be required in some circumstance before the voluminous datasets 200 of a patient are loaded. For example, we can think of the large number of image data resulting from a MR scan. It is therefore advantageous if all datasets 200 and the associated business logic processes 100, required for a medical task 10, need to be loaded only once.

According to an embodiment of the invention, it means that all existing datasets 200 and instances 112 of each business logic process 100 participating in the medical task 10, must be laded only once, for example as shown in FIG. 2 for a patient A admitted with abdominal cavity complaints. Thus, if a medical task 10 such as an abdominal cavity examination is ordered for a patient A, the dataset 200 for the patient A is loaded, along with all instances 112 of the business logic processes 100 which are involved in this medical task 10. Of course, if the medical tasks 10 must be realized for many patients then the required storage capacity is extremely high.

An embodiment of the present invention offers several strategies for executing the loading of the datasets 200 in a resource-saving manner. The one time loading of the business logic processes 100 and the datasets 200 for the patient, at the start of executing the task 10, means that maintenance is required only for this one-time loading. Following this, the datasets 200 and the instances 112 of the business logic processes 100 are preserved, so that they can be used immediately for the processing.

In particular, the results and datasets 200 of one step within the medical task 10, for example of a business logic process 100, are maintained over the course of more than one user interaction. This characteristic is typical for state-based applications. If these business logic processes 100 are not implemented as state-based applications, then the datasets would have to be loaded anew after each step within the medical task 10, meaning after executing each business logic process 100, which would unnecessarily increase the waiting time.

Executing the application as a stateful application is therefore advantageous. A central server 5000 is used for the execution and sequential control of the medical tasks 10.

Figure 3:
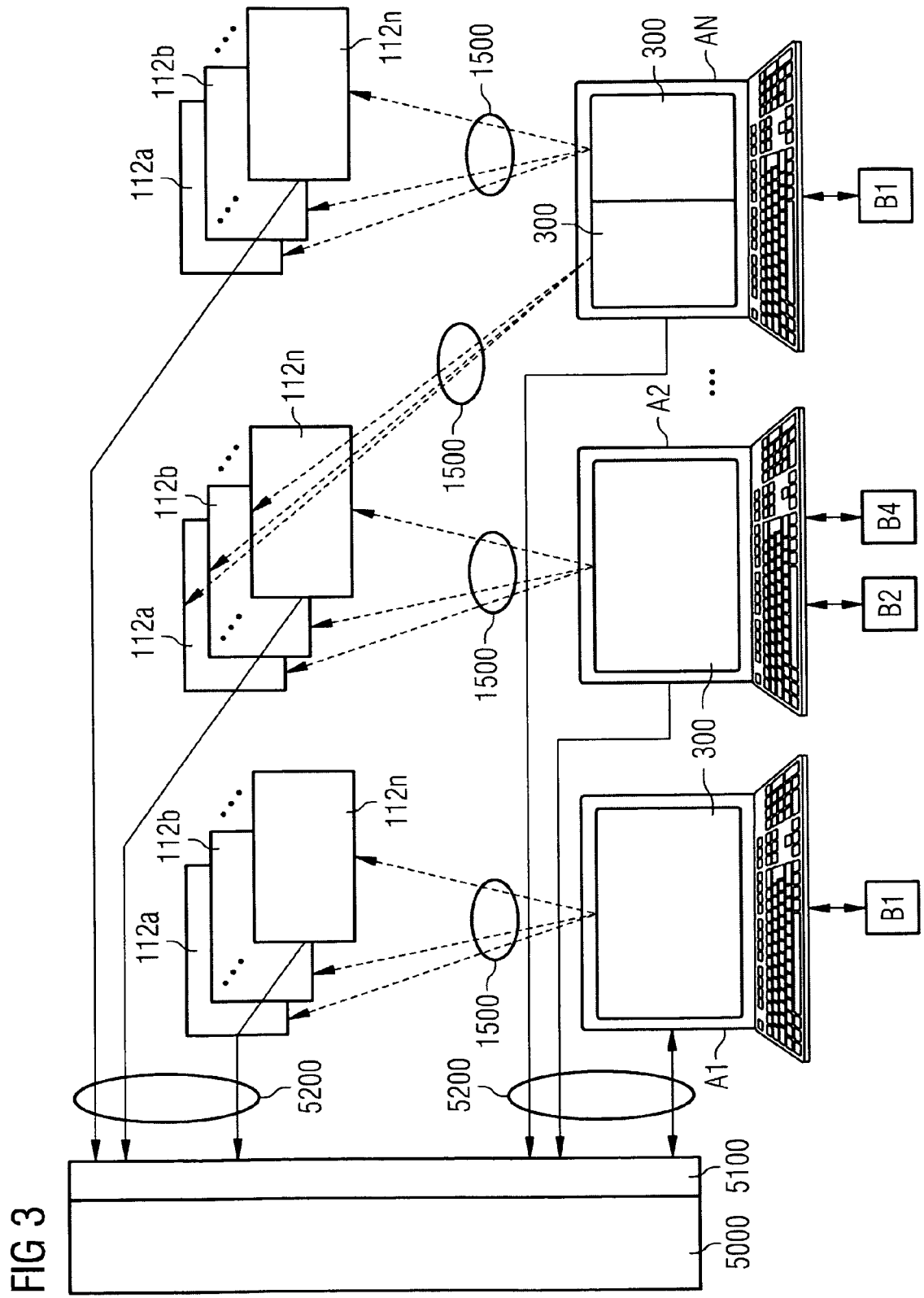
FIG. 3 shows an example embodiment of the present invention.

FIG. 3 shows an example in which n instances of a medical task 10 are started as instances 112a, 112b to 112n of the business logic process 100, meaning the instances 112a to 112n of the individual applications 11 within the medical task 10 are preserved simultaneously for all n patients and/or medical tasks 10.

If the medical task 10 is requested for a patient A, then the central server 5000 makes available the instances 112a of all business logic processes 100 participating in the medical tasks 10 for the patient A and loads the datasets 200 for the respectively relevant instances 112 of the business logic processes 100. For an instance 112a of the business logic 100 that may refer to the evaluation of the ultrasound data as shown in FIG. 2, for example, only ultrasound images must be loaded whereas it is generally not necessary to load MR data. Nevertheless, it is possible that an instance 112a of a business logic process 100 will relate to more than one result from a preceding application 11.

The central server 5000 can determine 1100 from a medical task 10 which applications 11 with their business logic processes 100 are required and can start the corresponding instances 112 for the business logic processes 100.

The central server 5000 comprises a control interface 5100, which allows it to exchange control messages 5200 with the instances 112 of the business logic processes 100. The concept of the container processes has proven to be advantageous in this connection. If a business logic process 100 is started for the first time, then a business logic container process for the business logic process 100 is initially started. The business logic container process is so-to-speak a cover (container) for executing the business logic processes 100 and/or the instances 112 of the business logic processes 100.

The concept of the business logic container process makes it possible to conduct all communication with the central server 5000 via the business logic container process. It also means that the business logic processes 100 can focus solely on the object to be solved, meaning on the step to be solved with the applications 11. All communication tasks are taken over by the business logic container process. The business logic process 100 can thus be embodied much leaner. The central server 5000 is furthermore able to dynamically interconnect 1400 the individual business logic processes 100, and thus also the instances 112 for the business logic processes 100, with the respective datasets 200, as indicated in FIG. 2.

As previously mentioned, it is possible for more than one instance 112 of a business logic process 100 to access data, for example heartbeat data.

Based on the 3-stage architecture for the application 11, shown in FIG. 1, it is furthermore necessary to start the presentation-logic processes 300 for a user in a specific user role B at a work station A in order to execute the business logic processes 100 and/or for the interaction with the user in the user role B. Typically, the user in the user role B, for example a MTA, would sit down and report in at a work station A, for example to evaluated ultrasound images.

Let's assume as example that the instances of the business logic processes 112*a* to 112*n* in the left column of FIG. 3 would correspond to the respective business logic processes 100 for evaluating ultrasound images. The MTA as example for a user in the user role B would have to start the presentation logic process 300 only once for evaluating the ultrasound images of the respective application 11.

The start-up of the presentation logic process 300 as a rule is tied to a brief flickering on the monitor. This flickering always occurs on prior art systems following the completion of a processing of a patient. The user generally considers this flickering unpleasant, especially since these work stations A typically are located in somewhat dark rooms. The user additionally looks intently at the monitor and a flashing or flickering on the monitor is considered disrupting.

An embodiment of the present invention therefore provides that the presentation logic process 300 for an application 11 advantageously must be started only once on a work station A. As soon as the presentation logic process 300 has been started, an embodiment of the present invention makes it possible to interconnect or link 1500 the presentation logic process 300 optionally with one of the instances 112 of the business logic process 100, as indicated with the dashed arrows in FIG. 3.

An embodiment of the present invention allows a user in the user role B to select which instance 112 of the business logic process 100 the user would like to process first. The user in the user role B could thus decide to process first the patient "Müller" and subsequently the patient "Meier," wherein a patient and/or an instance of a business logic process 100 could be selected from a work list. The work list indicates to the user how many instances 112 of the respective business logic processes 100 must still be processed, meaning they have not yet been interconnected 1500 with the presentation logic 300.

Since the presentation logic process 300 is already running on the work station A of the user, the monitor will not flash if the user changes from one business logic process 100 to the next one. In addition, the user is spared the long waiting times for loading the datasets 200, which are assigned to the instance 112 of the business logic process 100. Through interconnecting 1500, the user can change seamlessly from one instance 112*n* of a business logic process 100 to the following instance 112*b* of the business logic process 100 by using the presentation logic process 300. As a result, the execution of the application is simplified considerably for the user.

The central server 5000 can also exchange control messages 5200 with the work stations A via the control interface 5100. That is to say, the central server 5000 knows which work stations A are required to display at least one presentation logic process 300. The central server 5000 furthermore makes it possible to reserve the instances 112 of the business logic process 100 for the application 11 directly on the central server 5000 or on another computer and/or on the work station A. With the aid of the control messages 5200, the central server 5000 can always monitor the sequential control and the executing of the medical task 10 and the associated applications 11.

As furthermore indicated in FIG. 3 (in the center column), users in different user roles B, for example B2 and B4, can report in at the same work station A2 and can start the corresponding presentation logic processes 300, which they are authorized to start. It is also possible for a user in a user role B to start different presentation logic processes 300 at a work station A. For each presentation logic process 300 that is started, the invention provides a work list that indicates to the user the instances 112 which must still be processed.

In addition, the central server 5000 is in the position to show which applications 11 of the medical task 10 have already been realized and/or which must still be realized, meaning it is possible to find out via the central server 5000 whether or not a medical task 10 or a specific business logic process 100 of the task 10 has already been realized. The central server 5000 is therefore in a position to detect a status with respect to the sequential control and the execution of the medical task 10 and to indicate this status via a browser application. The status can comprise the following data: information on which presentation logic processes 300 run on which work stations A. It can furthermore contain information on which instances 112 of a business logic process 100 are interconnected with a presentation logic process 300, as well as information on how many instances 112 of a business logic process 100 have already been executed.

The central server 5000 is in the position to communicate via the control messages 5200 with the work stations A. Presentation logic container processes have proven to be advantageous for facilitating the communication between the central server 5000 and the presentation logic processes 300 running on the work stations A. These presentation logic container processes represent so-to-speak the master process for all running presentation logic processes 300. In other words, the presentation logic container process is a container for the executing of all presentation logic processes 300. It is the object of the presentation logic container process to ensure the communication with the central server 5000, meaning the presentation logic process 300 and/or the instances 112 of the business logic process 100 can run on different systems.

The present invention makes it possible to execute all instances 112 of the business logic process 100 on the central server 5000. However, it is also possible to use dedicated computers for executing all instances 112 of the business logic processes 100, which are provided within the process according to an embodiment of the invention. One variant provides that the central server 5000 and/or the instances 112 of the business logic processes 100 can be run on the work stations A. In extreme cases, an embodiment of the complete invention is executed at one work station A, provided this work station, and only this station, has sufficient resources.

A further goal of the invention is the extremely careful handling of the available resources for executing the medical tasks 10. An embodiment of the invention therefore provides heuristics that must be preserved in the same way as the instances 112 of the business logic processes 100.

An increasing number of medical tasks 10 also results in an increase in the number of running instances 112 for the applications 11 for a medical task 10. For a large number of patients, this can lead to performance problems since a large number of instances 112 of the business logic process 100 must be preserved simultaneously. It is possible in that case that an instance 112 of a business logic process 100, which has not been interconnected for an extended period of time with a presentation logic process 300, is made available for a different medical task 10, meaning especially for the medical task 10 for a different patient. For this, the central server 5000 can trigger the non-linked instance 112 of the business logic process 100 to persist in its state. It means that the state of the instance is stored, for example on a disk memory, such that the state of the instance 112 of the business logic process 100 can be regenerated from the stored information.

In the following step, it is possible to dynamically interconnect 1400 the datasets 200 of another patient, for whom the same application 11 must be run, with the non-used instance 112 of the business logic process 100. The central server 5000 is furthermore informed of the storage location for the previously not used business logic process 100 that persists in its state, so that the central server 5000 can access this storage location as needed to regenerate, if applicable, the state of the previously not used instance 112 of the business logic process 100 for the further processing.

It is furthermore possible to specify in the central server 5000 how many medical tasks 10 can be preserved with the respectively involved instances 112 of the business logic processes 100. If the number of preserved medical tasks 10 is sufficiently high, a user will notice a delay only during the first-time start-up of the presentation logic 300. For example, for the first 20 already preserved instances 112 of the applications 11, the user in the user role B can be interconnected 1500 with the respective, already preserved instances 112. It is only when processing a medical task 10 which is not preserved that the user must wait until the central server 5000 has loaded the corresponding instances 112 of the applications 11 and has dynamically interconnected 1400 the datasets 200 with the respective instances 112 of the business logic processes 100.

If the number of preserved medical tasks 10 with the respective instances 112 of the business logic processes 100 is too low, a user who would like to execute the individual applications 11 by using the business logic process 100 must frequently wait until the respective instances 112 of the suitable business logic processes 100 are started and the datasets 200 are dynamically interconnected 1400 with the instances 112. Of course, along with the number of preserved medical tasks 10, the costs also increase for using the process according to the invention and/or the costs increase for providing suitable hardware for the medical tasks 10.

Alternatively to the above-described strategy, it is possible to connect the presentation logic processes 300 rigidly with the associated business logic processes 100. In that case, the interconnecting 1500 between the presentation logic processes 300 and one of the suitable instances 112 of the business logic processes 100 can be omitted. In that case, we have an equal number of instances of the applications 11 (comprising the presentation logic process 300 and the business logic process 100) as there are users working with the system according to the invention, regardless of the number of medical tasks 10. This may be of interest in particular for smaller systems where in any case only a small number of users in a suitable user role B are available to process the medical tasks 10. Of course, the hardware is much cheaper for such an embodiment of the inventive process. At the same time, this cost saving is tied to longer waiting times during the changeover from one medical task 10 to another.

Figure 4:
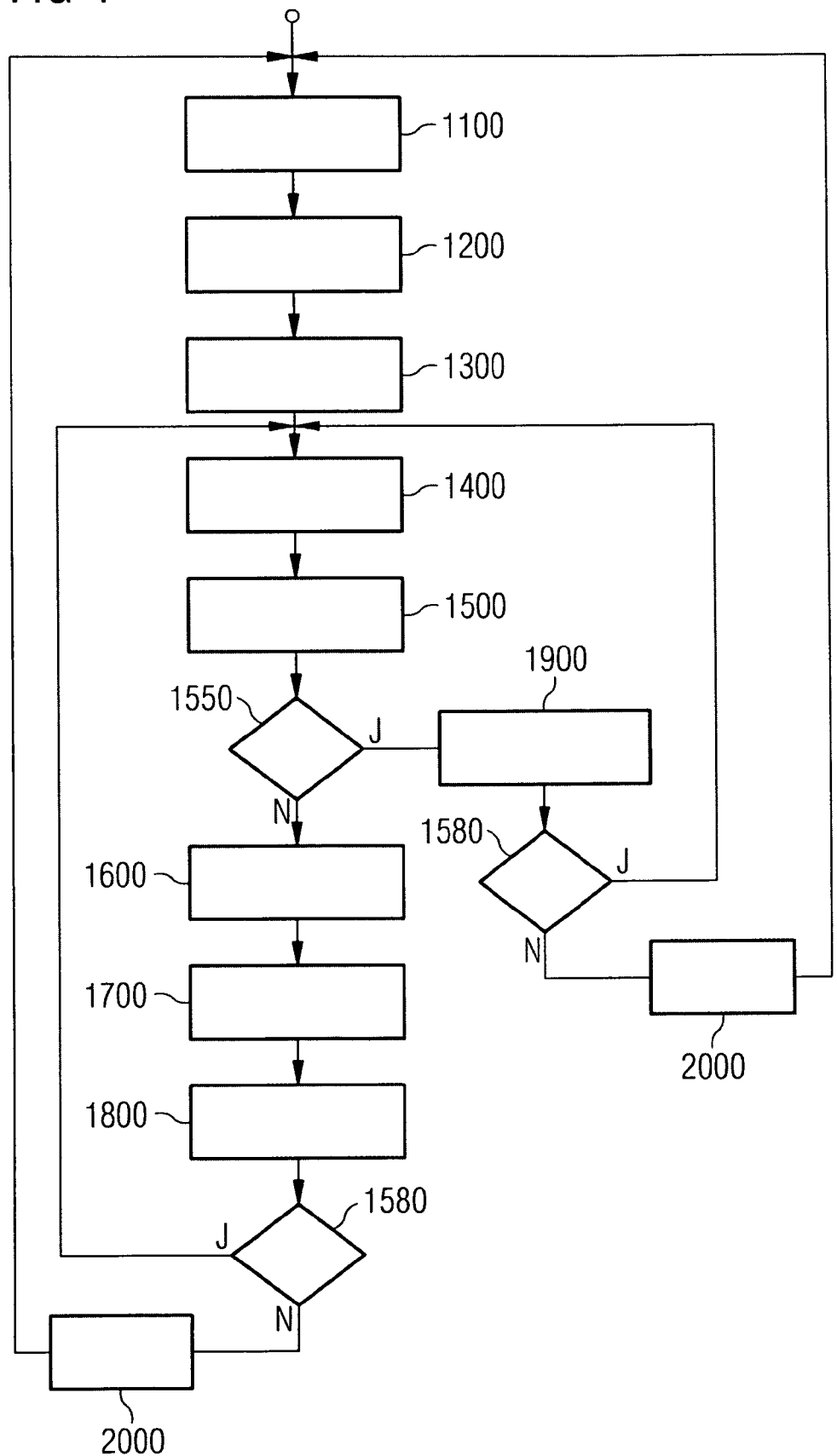
FIG. 4 shows a flow chart of the individual process steps according to one embodiment of the invention.

For realizing the inventive process, the central server 5000 executes a number of steps, which are shown in FIG. 4. In a step 1100, the central server 5000 determines the required applications 11 for a medical task 10, using its business logic processes 100. In step 1200, the central server 5000 determines the necessary datasets 200 for the medical task 10, then loads the required datasets 200 and makes these available to the business logic processes 100 and/or the instance 112 of the business logic processes.

This is followed by a step 1300 for determining the work stations A needed for executing the applications 11 of the medical task 10, on which at least one presentation logic process 300 is displayed, wherein this can follow, for example, from the registering of a user of a specific user role B at a work station A. For a MTA, for example, the central server 5000 determines the corresponding presentation logic processes 300, which are then started.

In a step 1400, the datasets 200 are dynamically interconnected 1400 with at least one instance 112 of a business logic process 100. It means for example that within a medical task 10, the heartbeats of a patient that were previously recorded with the first application 11 within the medical task 10 could be used by the second and fifth application 11 within the medical task 10. That is to say, in step 1400 and following the processing of the first application 11 within the medical task 10, the central server 5000 would dynamically interconnect 1400 the heartbeats with the instances 112 of the third and fifth applications 11. More precisely, the central server would dynamically interconnect 1400 the heartbeats with the instance 112 of the third and fifth business logic process 100. Owing to the dynamic interconnection 1400, the heartbeats in the selected example will be made available to the third and fifth application 11 within the medical task.

In a subsequent step 1500, the respective presentation logic process 300, for example started by the user in the user role B, is interconnected 1500 with at least one instance 112 of the business logic processes 100 of the application 11 within the medical task 10. In particular, an embodiment of the invention makes it possible to decide in an optional step 1550 whether an instance 112 for a business logic process 100 is not interconnected 1500 for a longer period of time with a presentation logic process 300.

The process according to an embodiment of the invention makes it possible for an instance 112 of a business logic process 100, which has not been in use for a longer period of time, to persist in its state during a step 1900. In a query 1580 it is then decided whether additional medical tasks 10 exist, which comprise the application 11 that has not been used for a longer period of time. If that is the case, the process is reversed in the J branch of the diagram shown in FIG. 5 before reaching the step 1400, and datasets 200 from a suitable medical task 10 are dynamically interconnected 1400 with the instance 112 of the business logic process 100. Insofar as no additional medical task 10 exists in step 1580, which comprises the application 11 that has not been used for a longer period of time, the instance 112 is first removed in step 2000 and the process returns to the start, so that the central server 5000 can decide which applications 11 with the associated business logic processes 100 must be started.

On the other hand, if the query in step 1550 is negative—meaning the instance 112 of the business logic process 100 from step 1500 was used—the business logic process 100 and the presentation logic process 300 are realized in step 1600. The business logic process 100 and the presentation logic process 300 can then be executed at the specified work station A. Alternatively, it is also possible to keep the business logic processes 100 available on the central server 5000 and/or on a specialized hardware, which is connected to the central server 5000 and the specified work station A. As soon as the application 11 is executed, a query is posed in step 1580 to determine whether additional medical tasks 10 are present, which comprise the same applications 11. If this is the case, the process returns to the point before step 1400. If this is not the case, then the instance 112 of the business logic process 100 is initially removed during the step 2000 and the process returns to the start to load a new medical task if applicable.

So far, an embodiment of the invention has been illustrated in connection with the inventive process for the sequential control and the execution of a medical task 10. An embodiment of the invention furthermore also relates to a system for executing the process according to an embodiment of the invention.

The block diagram in FIG. 5 provides an overview over the system according to an embodiment of the invention. In addition to the central server 5000, the system comprises a task interface 1020, which is designed to accept a number of different applications 11 for a task. For example, this could be the interface for triggering a new task 10 for a patient. We also want to point out in this connection that the datasets 200 are patient-specific and can comprise several files. The system also comprises an application determination module 1120.

With the aid of the application determination module 1120, the central server 5000 can determine which applications 11 with the respective business logic processes 100 are required for the medical task 10. In other words, the application determination module 1120 performs an analysis of the task 10 accepted in the task interface 1020.

All applications 11 required for executing the medical task 10 are thus known to the central server 5000. The system furthermore comprises a dataset determination module 1220. With the aid of control messages 5200, the dataset determination module 1220 is used to load suitable datasets 200 that are required for the medical task 10. These required datasets 200 are loaded exactly once by the dataset determination module 1220 and are made available to the application 11, meaning to the business logic processes 100 and/or their instances 112.

The system also comprises a work station determination module 1320, which is connected via control messages 5200 to the work stations A. The work station determination module 1320 is used to determine the work stations A required for executing the application 11. With the aid of a dynamic interconnecting module 1420, the datasets 200 that are made available by the dataset determination module 1220 are dynamically interconnected 1400 with at least one instance 112 of a business logic process 100. As previously mentioned, it can be useful for the medical task 10 if datasets 200, for example involving heartbeats, are made available to several business logic processes 100, meaning to an instance 112 of at least one business logic process 100 by using the dynamic interconnecting module 1420.

The system also comprises an interconnecting module 1520. The module 1520 is intended for interconnecting 1500 with at least one instance in the business logic process 100 of the specific application 11. The system furthermore comprises an execution module 1620, which is designed for executing 1600 the specific business logic processes 100 and the presentation logic processes 300 at the specified work stations A. In addition, the system comprises a storage module 1720 for storing 1700 the datasets 200, following the executing of the application 11 by the execution module 1620.

Finally, we want to point out that the description of example embodiments of the invention should in principle not be understood to restrict to a specific physical realization of the invention. In particular, it is obvious to one skilled in the art that the invention can be realized in part or completely with software and/or hardware and/or distributed over several physical products, in particular also with computer program products.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

REFERENCE LIST

A work station
10 medical tasks
11 application
B user
200 datasets
100 business logic process
112 instance of a business logic process 100
300 presentation logic process
1100 determination of applications 11
1120 application determination module
1200 determination of datasets 200
1220 dataset determination module
1020 task interface
1300 determination of required work stations
1320 work station determination module
1400 dynamic interconnection or linking of datasets 200
1420 dynamic interconnection module
1500 interconnecting of the presentation logic process 300
1520 interconnecting module
1550 query as to whether or not used
1580 query as to whether additional tasks 10 comprise business logic process 100
1600 executing of business logic processes 100 and presentation logic processes 300
1620 execution module
1700 storing of datasets 200
1720 storage module
1800 transmitting datasets 200 to following business logic processes 100
1900 persisting in the state
2000 removing of the business logic process logo 100

What is claimed is:

1. A process for sequential control and execution of a medical task, processed with a plurality of different, computer-implemented, medical-technical, stateful applications, the medical-technical applications being respectively based on a multi-layer software architecture including a data layer with a number of different datasets; a business logic layer with a number of business logic processes, a business logic process implementing respectively one application and several instances of a business logic process being realizable; a presentation layer with a number of presentation logic processes for displaying datasets within the framework of executing the associated business logic processes, wherein a central server performs:
   determining the medical-technical application and business logic processes for the medical task;
   determining the datasets for the medical task;
   one-time loading of the determined datasets such that the determined datasets are made available to all instances of different business logic processes without further loading of the determined datasets;
   dynamically interconnecting the loaded datasets with at least one instance of a business logic process or with an instance of at least one business logic process, each business logic process or instance of the business logic process being assigned to a single patient;
   determining work stations for processing the determined medical-technical application, on which at least one presentation logic process is to be displayed;
   interconnecting the respective presentation logic process of the respectively determined medical-technical application with at least one instance of the business logic process of the determined medical-technical application; and
   executing the determined business logic processes and the presentation logic processes and storing the datasets, wherein
      respectively one presentation logic process is displayed on at least one work station,
      respectively one work station displays at least one presentation logic process, and
      following the execution of a business logic process, the datasets processed by the business logic process are stored automatically and are transmitted to at least one of the business logic processes within the task for a further execution of the task, without having to load the datasets anew.

2. The process according to claim 1, wherein each medical-technical application is furthermore assigned at least one user role and wherein at least one user in this user role is authorized to at least one of start and execute the presentation logic process of the medical-technical application.

3. The process according to claim 2, wherein the at least one user role of the user authorizes the dynamic interconnecting of the presentation logic process with the business logic process of the same user role.

4. The process according to claim 3, wherein a work list is displayable for a user in a user role.

5. The process according to claim 2, wherein a work list is displayable for a user in a user role.

6. The process according to claim 1, wherein a status is detected with respect to the sequential control and the executing of the medical task, which can be called up via a browser application.

7. The process according to claim 6, wherein the status comprises the following information:
information on which presentation logic processes run on which work station;
information relating to which instances of a business logic process are interconnected with a presentation logic process; and
information on at least one of how many instances of a business logic process and how many business logic processes of a task have already been processed.

8. The process according to claim 6, wherein the status is processed further by the central server.

9. The process according to claim 7, wherein the status is processed further by the central server.

10. The process according to claim 1, wherein a task overview is at least one of provided and displayed during the selection of a medical task, which comprises the following information:
at least one of which business logic processes for meeting the task are loaded at the present time and which business logic processes for meeting the task must still be loaded; and
at least one of which datasets for executing the medical task are loaded at the present time and which datasets for executing the medical task must still be loaded.

11. The process according to claim 1, wherein all process steps are realized automatically.

12. The process according to claim 1, wherein all medical tasks, datasets, business logic processes, presentation logic processes, work stations and at least one of the interconnecting and the dynamic interconnecting are managed in the central server.

13. The process according to claim 1, wherein the central server is able to at least one of add, delete and modify at least one of presentation logic processes and business logic processes.

14. The process according to claim 1, wherein the central server comprises a control interface for exchanging control messages.

15. The process according to claim 1, wherein a business logic container process is provided for the communication between the respective business logic process and the central server, and for loading the business logic processes, and wherein a presentation logic container process is provided for the communication between the respective presentation logic process with the central server and for loading the presentation logic processes.

16. The process according to claim 1, wherein at least one of the interconnecting and the dynamic interconnecting is monitored.

17. The process according to claim 16, wherein it is monitored whether, and if applicable, for how long a business logic process is not interconnected with a presentation logic process, so that the non-interconnected business logic process is useable for a different medical task, if necessary, and is dynamically interconnectable, wherein the state of the non-interconnected business logic process is confirmed.

18. The process according to claim 1, wherein the interconnecting between the respective presentation logic process and an associated business logic process occurs based on a pre-configured diagram.

19. The process according to claim 1, wherein a maximum number of medical tasks are determined, which are executable in parallel by the central server.

20. The process according to claim 1, wherein the central server is run at least in part on a work station.

21. The process according to claim 1, wherein the dataset, which is necessary for executing the respective business logic process, is provided on the central server and not on the respective work station on which the presentation logic process for the business logic process is loaded.

22. The process according to claim 1, wherein the dataset is patient-specific and comprises different electronic files.

23. The process according to claim 1, wherein the dataset that is generated or changed by respectively one business logic process is automatically stored and transmitted to at least one the following business logic processes within the task.

24. The process according to claim 1, wherein at least one of the business logic processes, the instances of the business logic processes and the presentation logic processes are executed on the central server.

25. A system for the sequential control and execution of a medical task, which is processed with a plurality of different, computer-implemented, medical-technical, stateful applications, the system comprising:
a task interface, designed to accept a number of different medical-technical applications for a medical task, wherein the medical-technical applications are respectively based on a 3-layer architecture composed of
a data layer having a number of different datasets,
a business logic layer with a number of business logic processes, wherein respectively one business logic process implements one medical-technical application and wherein several instances of a business logic process are executable, each business logic process or instance of the business logic process being assigned to a single patient, and
a presentation layer with a number of presentation logic processes for displaying datasets within the framework of executing the associated business logic processes; and
a central server, the central server including,
an application determination module designed to determine the medical-technical applications and business logic processes for executing the medical task,
a dataset determination module designed to determine the datasets for realizing the medical task, the dataset determination module being further designed to perform one-time loading of the determined datasets such that the determined datasets are available to all instances of different business logic processes without further loading of the determined datasets,
a work station determination module designed to determine work stations necessary for executing the determined medical-technical application and on which at least one presentation logic process is to be displayed,
a dynamic interconnection module designed for dynamic interconnection of the loaded datasets with precisely one instance of a business logic process,
an interconnection module designed for interconnecting the respective presentation logic processes of the respectively determined medical-technical application with at least one instance of the business logic process for the determined medical-technical application,
an execution module designed for executing the business logic processes and the presentation logic processes at the specified work stations, and a storage module designed to store the datasets, wherein respectively one presentation logic process is displayed on at least one work station and on each work station at least one presentation logic process is displayed, and following the execution of a business logic process, the datasets that are processed by the business logic processes are automatically stored and are transmitted to at least one business logic processes for the further execution, without having to load the datasets anew.

26. A computer program product which, in accordance with claim 1, implements a process for the sequential control and execution of a medical task that is processed with a plurality of different, computer-implemented, medical-technical, stateful applications when the computer program product is executed on at least one of a computer unit and a work station.

27. A computer readable medium including program segments for, when executed on a computer device, causing the computer device to implement the method of claim 1.

* * * * *

UNITED STATES PATENT AND TRADEMARK OFFICE
CERTIFICATE OF CORRECTION

| | | |
|---|---|---|
| PATENT NO. | : 8,392,218 B2 | Page 1 of 1 |
| APPLICATION NO. | : 12/382528 | |
| DATED | : March 5, 2013 | |
| INVENTOR(S) | : Detlef Becker et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 735 days.

Signed and Sealed this
Second Day of December, 2014

Michelle K. Lee
*Deputy Director of the United States Patent and Trademark Office*